(12) United States Patent
Fujita et al.

(10) Patent No.: US 11,866,354 B2
(45) Date of Patent: Jan. 9, 2024

(54) EXTRACT OF PLANT POWDER, AND WATER PURIFIER

(71) Applicant: Dexerials Corporation, Tokyo (JP)

(72) Inventors: Takanori Fujita, Tokyo (JP); Ryu Shimada, Tokyo (JP); Masahiko Ito, Tokyo (JP); Masato Hasegawa, Tokyo (JP)

(73) Assignee: DEXERIALS CORPORATION, Tokyo (JP)

(*) Notice: Subject to any disclaimer, the term of this patent is extended or adjusted under 35 U.S.C. 154(b) by 82 days.

(21) Appl. No.: 17/410,356

(22) Filed: Aug. 24, 2021

(65) Prior Publication Data

US 2021/0380444 A1    Dec. 9, 2021

Related U.S. Application Data

(62) Division of application No. 16/333,440, filed as application No. PCT/JP2017/032941 on Sep. 12, 2017.

(30) Foreign Application Priority Data

Sep. 16, 2016   (JP) .................. 2016-181619
Sep. 11, 2017   (JP) .................. 2017-174021

(51) Int. Cl.
  *C02F 1/52*       (2023.01)
  *B01D 21/01*      (2006.01)
  (Continued)

(52) U.S. Cl.
  CPC ............ *C02F 1/5263* (2013.01); *B01D 21/01* (2013.01); *B01J 20/22* (2013.01); *C02F 1/286* (2013.01);
  (Continued)

(58) Field of Classification Search
  None
  See application file for complete search history.

(56) References Cited

U.S. PATENT DOCUMENTS

2006/0216362 A1    9/2006   Enoki et al.
2007/0112183 A1    5/2007   Kitano et al.
(Continued)

FOREIGN PATENT DOCUMENTS

CN    102247814 A    11/2011
CN    102432692 A     5/2012
(Continued)

OTHER PUBLICATIONS

Timpa (J. Agric. Food Chem., 1991, 39, 270-275). (Year: 1991).*
(Continued)

*Primary Examiner* — Clare M Perrin
(74) *Attorney, Agent, or Firm* — BUCHANAN INGERSOLL & ROONEY PC

(57) ABSTRACT

Provided are an extract, which is a fractionated component 1 of a water extract of a plant powder, wherein the fractionated component 1 is a fractionated component having a fractionation molecular weight of 12,000 or greater, wherein an ethanol-undissolved component of the fractionated component 1 exhibits a peak attributable to carboxylic acid in a Fourier transform infrared spectroscopy (FT-IR) measurement and exhibits a peak attributable to cellulose in a gas chromatography mass spectrometry (GC-MS) measurement, and wherein an ethanol-dissolved component of the fractionated component 1 exhibits a peak attributable to carboxylic acid in the FT-IR measurement and exhibits a peak attributable to a plant protein in the GC-MS measurement, and a water-purifying agent containing the extract.

6 Claims, 11 Drawing Sheets

(51) Int. Cl.

| | |
|---|---|
| *B01J 20/22* | (2006.01) |
| *C02F 1/28* | (2023.01) |
| *C02F 1/56* | (2023.01) |
| *A61K 8/73* | (2006.01) |
| *A61K 31/722* | (2006.01) |
| *A61K 47/36* | (2006.01) |
| *A61K 47/69* | (2017.01) |
| *A61K 49/18* | (2006.01) |
| *C02F 101/10* | (2006.01) |
| *C02F 101/14* | (2006.01) |
| *C02F 101/20* | (2006.01) |
| *C02F 101/22* | (2006.01) |

(52) U.S. Cl.
CPC .............. *C02F 1/5272* (2013.01); *C02F 1/56* (2013.01); *A61K 8/73* (2013.01); *A61K 31/722* (2013.01); *A61K 47/36* (2013.01); *A61K 47/6939* (2017.08); *A61K 49/1863* (2013.01); *C02F 2101/103* (2013.01); *C02F 2101/14* (2013.01); *C02F 2101/20* (2013.01); *C02F 2101/203* (2013.01); *C02F 2101/22* (2013.01)

(56) References Cited

U.S. PATENT DOCUMENTS

| | | | |
|---|---|---|---|
| 2013/0299433 A1* | 11/2013 | Inagaki | B01J 20/24 210/730 |
| 2014/0353257 A1 | 12/2014 | Cuero Rengifio et al. | |
| 2015/0126619 A1 | 5/2015 | Varum et al. | |
| 2017/0291835 A1 | 10/2017 | Kimura et al. | |

FOREIGN PATENT DOCUMENTS

| | | | |
|---|---|---|---|
| CN | 103641936 | A | 3/2014 |
| CN | 104562632 | A | 4/2015 |
| EP | 1348717 | A2 | 10/2003 |
| JP | 03041014 | A | 2/1991 |
| JP | 07069910 | A | 3/1995 |
| JP | 07070208 | A | 3/1995 |
| JP | 11060607 | A | 3/1999 |
| JP | 11114313 | A | 4/1999 |
| JP | 2000140509 | A | 5/2000 |
| JP | 2008126168 | A | 6/2008 |
| JP | 2011-194384 | A | 10/2011 |
| JP | 2011194385 | A | 10/2011 |
| JP | 2014008428 | A | 1/2014 |
| JP | 2016073898 | A | 5/2016 |
| JP | 2016153470 | A | 8/2016 |
| TW | 201615562 | A | 5/2016 |
| WO | 2004/100969 | A1 | 11/2004 |

OTHER PUBLICATIONS

Xie et al. (Food Chemistry, 2010, 119, 1626-1632). (Year: 2010).*
First Notification of Office Action dated Nov. 27, 2020, by the Patent Office of the People's Republic of China in corresponding Chinese Patent Application No. 201780057054.3, and an English translation of the Notification. (27 pages).
International Search Report (PCT/ISA/210) dated Nov. 7, 2017, by the Japanese Patent Office as the International Searching Authority for International Application No. PCT/JP2017/032941.
Notice of Reasons for Rejection dated Mar. 9, 2021, by the Japanese Patent Office in corresponding Japanese Patent Application No. 2017-174021 and an English translation of the Notice. (19 pages).
Office Action dated Feb. 8, 2021, by the Taiwanese Patent Office in corresponding Taiwanese Patent Application No. 106131858 and an English translation of the Office Action. (11 pages).
PCT/IPEA/408 dated Sep. 18, 2018, for International Application No. PCT/JP2017/032941.
PCT/IPEA/409 dated Sep. 16, 2016, for International Application No. PCT/JP2017/032941.
Tetsuji Okuda, "Practical Purification of Coagulation Active Component Extracted from Moringa oleifera seeds by Salt Solution and Its Performance", Proceedings of Environmental and Engineering Research, 2006, vol. 43, pp. 605-610.
Extended European Search Report dated May 6, 2020, by the European Patent Office in corresponding European Patent Application No. 17850893.3. (7 pages).
Written Opinion (PCT/ISA/237) dated Nov. 7, 2017, by the Japanese Patent Office as the International Searching Authority for International Application No. PCT/JP2017/032941.
Office Action (First Notification of Office Action) dated Sep. 29, 2022, by the State Intellectual Property Office of People's Republic of China in corresponding Chinese Patent Application No. 202110551615.3 and an English translation of the Office Action. (17 pages).
Office Action dated Dec. 6, 2022, by the U.S. Patent and Trademark Office in U.S. Appl. No. 16/333,440. (12 pages).
Office Action dated Feb. 14, 2022, by the U.S. Patent and Trademark Office in related U.S. Appl. No. 16/333,440. (10 pages).
Office Action dated May 3, 2022, by the U.S. Patent and Trademark Office in U.S. Appl. No. 16/333,440, U.S. Patent and Trademark Office, Alexandria, VA. (10 pages).
Notice of Reasons for Refusal dated Sep. 14, 2021, by the Japanese Patent Office in corresponding Japanese Patent Application No. 2017-174021, and an English translation of the Notice. (12 pages).
Office Action issued by the U.S. Patent and Trademark Office dated Aug. 31, 2021, by the U.S. Patent and Trademark Office in U.S. Appl. No. 16/333,440. (8 pages).
Office Action dated Jul. 29, 2022, by the U.S. Patent and Trademark Office in U.S. Appl. No. 16/333,440. (9 pages).
Office Action issued by the U.S. Patent and Trademark Office dated Dec. 3, 2021, by the U.S. Patent and Trademark Office in U.S. Appl. No. 16/333,440. (7 pages).
Chitoceuticals, p. 1, accessed online at https://www.gmp-chitosan.com/downloads/specifications/Chitoceuticals/Chitosan%20Oligomer/44009-chitoceuticals-chitosan-oligomer.pdf (Year: 2011).
Office Action (Second Notification of Office Action) dated Mar. 14, 2023, by the Patent Office of the People's Republic of China in corresponding Chinese Patent Application No. 202110551615.3, and an English translation of the Office Action. (16 pages).
Office Action (Notice of Reasons for Refusal) dated Jul. 25, 2023, by the Japan Patent Office in corresponding Japanese Patent Application No. 2022-105219 and an English translation of the Office Action. (9 pages).
Office Action dated Sep. 15, 2023, by the U.S. Patent and Trademark Office in U.S. Appl. No. 18/177,182 (11 pages).

* cited by examiner

"Intermediate jute No. 3": identification number Varieties Identification of Registration No1209006in Anhui province "Intermediate kenaf": identification number Varieties Identification of Registration No1209001 in Anhui province

EXTRACT OF PLANT POWDER, AND WATER PURIFIER

CROSS-REFERENCE TO RELATED APPLICATIONS

This application is a division of U.S. patent application Ser. No. 16/333,440, filed on Mar. 14, 2019, which is a national stage of International Patent Application No. PCT/JP2017/032941, filed on Sep. 12, 2017, which in turn claims priority to Japanese Patent Application No. 2017-174021, filed on Sep. 11, 2017, and Japanese Patent Application No. 2016-181619, filed on Sep. 16, 2016, the entire disclosures of all of which are incorporated herein by reference.

TECHNICAL FIELD

The present invention relates to a plant powder extract and a water-purifying agent containing the extract, both used for purification of water such as industrial wastewater.

BACKGROUND ART

In recent years, large amounts of waste liquids including environmentally hazardous substances such as metal ions and fluorine ions as inorganic ions have been generated in the processes for producing various products in plants.

Meanwhile, regulations on effluence of such inorganic ions have been becoming gradually strict. In order to comply with the effluent control, an inorganic ion removing method that can effectively remove inorganic ions from wastewater including the inorganic ions and can be carried out as easily and inexpensively as possible is demanded.

Hitherto, as the method for removing impurity ions from, for example, wastewater from plants, for example, a flocculating precipitation method, an ion-exchange method, a method for adsorption to an adsorbent such as activated charcoal, an electrosorption method, and a magnetic adsorption method have been proposed.

For example, as the flocculating precipitation method, there has been proposed a method of performing a step of adding a base to wastewater in which heavy metal ions are dissolved, to make the wastewater basic, insolubilize at least part of the heavy metal ions, and form a suspended solid matter, a step of adding an inorganic flocculant to the wastewater to make the suspended solid matter flocculate and settle, a step of adding a polymeric flocculant to the wastewater to turn the suspended solid matter to a macro-floc, and an adsorbing step of passing the wastewater through an adsorption layer containing a cation exchanger formed of a leafy vegetable such as mulukhiya and Japanese mustard spinach (see, e.g., PTL 1).

There has also been proposed a flocculating method of flocculating and separating particles in a suspension by means of mixed use or combined use of a flocculant containing at least any one of mulukhiya, a dried product of mulukhiya, and an extract of mulukhiya with a polymeric flocculant (see, e.g., PTL 2).

There have also been proposed a water-purifying agent formed of a granulated substance containing a mixture of a plant powder and a polymeric flocculant, and a water-purifying method using the water-purifying agent (see, e.g., PTL 3).

However, although it hitherto has been known that plant powders can be used for water purification of wastewater, what contribute to water purification, or the specific contributing components have not been elucidated. Hence, there is a matter of study left in use of plant powders for water purification of wastewater.

CITATION LIST

Patent Literature

PTL 1: Japanese Patent Application Laid-Open (JP-A) No. 2011-194385
PTL 2: JP-A No. 11-114313
PTL 3: JP-A No. 2016-73898

SUMMARY OF INVENTION

Technical Problem

The present invention has an object to identify effective components in plant powders that contribute to water purification and provide a water-purifying agent that can exhibit an excellent water-purifying performance to wastewater efficiently even in a small amount and infallibly.

Solution to Problem

Means for solving the above problems are as follows.
<1> An extract, being formed of:
  a fractionated component 1 (hereinafter, may also be referred to as component 1 in the present invention) of a water extract of a plant powder,
  wherein the fractionated component 1 is a fractionated component having a fractionation molecular weight of 12,000 or greater,
  wherein an ethanol-undissolved component of the fractionated component 1 exhibits a peak attributable to carboxylic acid in a Fourier transform infrared spectroscopy (FT-IR) measurement and exhibits a peak attributable to cellulose in a gas chromatography mass spectrometry (GC-MS) measurement, and
  wherein an ethanol-dissolved component of the fractionated component 1 exhibits a peak attributable to carboxylic acid in the FT-IR measurement and exhibits a peak attributable to a plant protein in the GC-MS measurement.
<2> The extract according to <1>,
  wherein the ethanol-undissolved component and the ethanol-dissolved component of the fractionated component 1 exhibit the peaks near 1,700 (cm$^{-1}$) and near 1,600 (cm$^{-1}$) in the FT-IR measurement.
<3> The extract according to <1> or <2>,
  wherein the fractionated component 1 contains a substance having a weight average molecular weight (Mw) of 300,000 or greater by 50% or greater.
<4> The extract according to any one of <1> to <3>,
  wherein the plant powder is a powder of *Corchorus olitorius*.
<5> An extract, being formed of:
  a fractionated component 2 (hereinafter, may also be referred to as component 2 in the present invention) of a water extract of a plant powder,
  wherein the fractionated component 2 is a fractionated component having a fractionation molecular weight of less than 3,400,
  wherein an ethanol-undissolved component of the fractionated component 2 exhibits a peak attributable to an amide group in a FT-IR measurement, and wherein an ethanol-dissolved component of the fractionated component 2 exhibits a peak attributable to an amide group in the FT-IR measurement.

<6> The extract according to <5>,
wherein the ethanol-undissolved component and the ethanol-dissolved component of the fractionated component 2 exhibit main peaks in a range of from 1,590 (cm$^{-1}$) through 1,630 (cm$^{-1}$) in the FT-IR measurement.

<7> The extract according to <5> or <6>,
wherein the ethanol-undissolved component and the ethanol-dissolved component of the fractionated component 2 exhibit peaks of 1,8-diazacyclotetradecane-2,7-dione in a GC-MS measurement.

<8> The extract according to any one of <5> to <7>,
wherein the fractionated component 2 contains a substance having a weight average molecular weight (Mw) of from 200 through 2,500 by 90% or greater.

<9> The extract according to any one of <5> to <8>,
wherein the fractionated component 2 is a water-soluble chitosan.

<10> The extract according to any one of <5> to <9>,
wherein the plant powder is a powder of *Corchorus olitorius*.

<11> A water-purifying agent, including:
the extract according to any one of <1> to <4>.

<12> A water-purifying agent, including:
the water-purifying agent according to <11>; and
the extract according to any one of <5> to <10>.

<13> A water-purifying agent, including:
the extract according to any one of <5> to <10>.

<14> A water-purifying agent, including:
a plant powder,
wherein when the plant powder is subjected to water extraction, an extracted component, which is formed of a fractionated component 1 having a fractionation molecular weight of 12,000 or greater, is contained in the plant powder in an amount of 0.5% by mass or greater,
wherein an ethanol-undissolved component of the fractionated component 1 exhibits a peak attributable to carboxylic acid in a FT-IR measurement and exhibits a peak attributable to cellulose in a GC-MS measurement, and
wherein an ethanol-dissolved component of the fractionated component 1 exhibits a peak attributable to carboxylic acid in the FT-IR measurement and exhibits a peak attributable to a plant protein in the GC-MS measurement.

<15> The water-purifying agent according to <14>,
wherein the ethanol-undissolved component and the ethanol dissolved component of the fractionated component 1 exhibit the peaks near 1,700 (cm$^{-1}$) and near 1,600 (cm$^{-1}$) in the FT-IR measurement.

<16> The water-purifying agent according to <14> or <15>,
wherein the fractionated component 1 contains a substance having a weight average molecular weight (Mw) of 300,000 or greater by 50% or greater.

<17> The water-purifying agent according to any one of <14> to <16>,
wherein the plant powder is a powder of *Corchorus olitorius*.

<18> A water-purifying agent, including:
a plant powder,
wherein when the plant powder is subjected to water extraction, an extracted component, which is formed of a fractionated component 2 having a fractionation molecular weight of less than 3,400, is contained in the plant powder in an amount of 0.05% by mass or greater,
wherein an ethanol-undissolved component of the fractionated component 2 exhibits a peak attributable to an amide group in a FT-IR measurement, and
wherein an ethanol-dissolved component of the fractionated component 2 exhibits a peak attributable to an amide group in the FT-IR measurement.

<19> The water-purifying agent according to <18>,
wherein the ethanol-undissolved component and the ethanol-dissolved component of the fractionated component 2 exhibit main peaks in a range of from 1,590 (cm$^{-1}$) through 1,630 (cm$^{-1}$) in the FT-IR measurement.

<20> The water-purifying agent according to <18> or <19>,
wherein the ethanol-undissolved component and the ethanol-dissolved component of the fractionated component 2 exhibit peaks of 1,8-diazacyclotetradecane-2,7-dione in a GC-MS measurement.

<21> The water-purifying agent according to any one of <18> to <20>,
wherein the fractionated component 2 contains a substance having a weight average molecular weight (Mw) of from 200 through 2,500 by 90% or greater.

<22> The water-purifying agent according to any one of <18> to <21>,
wherein the fractionated component 2 is a water-soluble chitosan.

<23> The water-purifying agent according to any one of <18> to <22>,
wherein the plant powder is a powder of *Corchorus olitorius*.

<24> The water-purifying agent according to any one of <14> to <17>,
wherein the water-purifying agent is the water-purifying agent according to any one of <18> to <23>.

<25> The water-purifying agent according to any one of <11> to <24>, including:
a polymeric flocculant.

<26> The water-purifying agent according to <25>,
wherein the polymeric flocculant is polyacrylamide.

<27> A wastewater treatment method, including:
feeding the water-purifying agent according to any one of <11> to <26> to wastewater, to remove an inorganic unnecessary substance in the wastewater.

<28> The wastewater treatment method according to <27>,
wherein the wastewater is wastewater including the inorganic unnecessary substance containing at least any one selected from the group consisting of nickel, fluorine, iron, copper, zinc, chromium, arsenic, cadmium, tin, and lead.

Advantageous Effects of Invention

The present invention can provide a water-purifying agent that can exhibit an excellent water-purifying performance to wastewater efficiently even in a small amount and infallibly.

DESCRIPTION OF EMBODIMENTS (Extract of Plant Powder)

As a result of earnest studies into the water-purifying function of a plant powder, the present inventors have found effective components of a plant powder that contribute to water purification.

Figure 1:
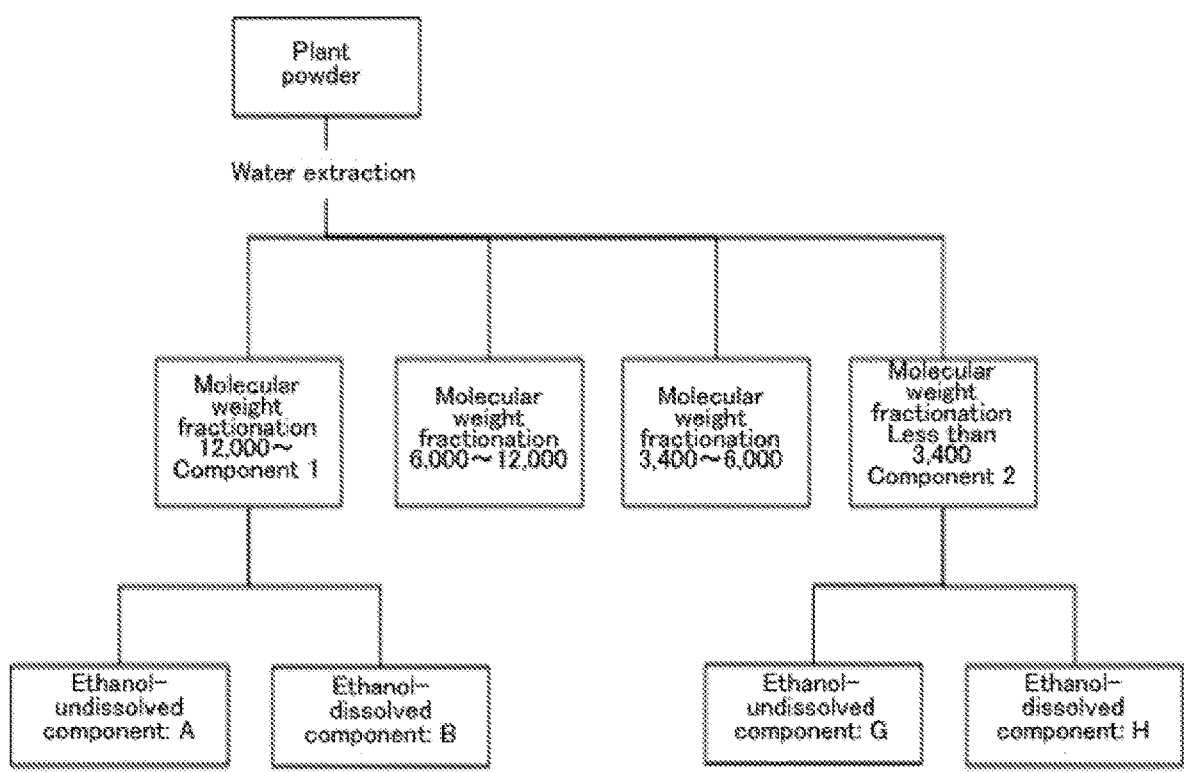
FIG. 1 is an image diagram illustrating a fractionated component 1 (may also be referred to as component 1) and a fractionated component 2 (may also be referred to as component 2), which are the subjects of the present invention among water extracts of a plant powder.

It has been confirmed that among water extracts of the plant powder, extracted components, which are formed of a fractionated component 1 (may also be referred to as component 1 in the present invention) having a fractionation molecular weight of 12,000 or greater and a fractionated component 2 (may also be referred to as component 2 in the present invention) having a fractionation molecular weight of less than 3,400 illustrated in FIG. 1, each have an excellent water-purifying action.

Here, the plant is not particularly limited and any plant that contains the component 1 and the component 2 in effective amounts respectively may be used. Preferable examples of the plant include Corchorus olitorius and mulukhiya.

Particularly, as Corchorus olitorius, for example, Corchorus olitorius produced in Nansha City of China, or "intermediate jute No. 4" under nationally identified hemp 2013, "intermediate jute No. 3" under varieties identification of registration No. 1209006 in Anhui province, "intermediate jute No. 1" under XPD005-2005, and "intermediate kenaf" under varieties identification of registration No. 1209001 in Anhui province, which are identification numbers in Institute of Bast Fiber Crops, Chinese Academy of Agricultural Sciences, can be suitably used.

Above all, the "intermediate jute No. 4", the "intermediate jute No. 3", and the "intermediate kenaf" are more preferable, and the "intermediate jute No. 4" is particularly preferable.

Figure 8A:
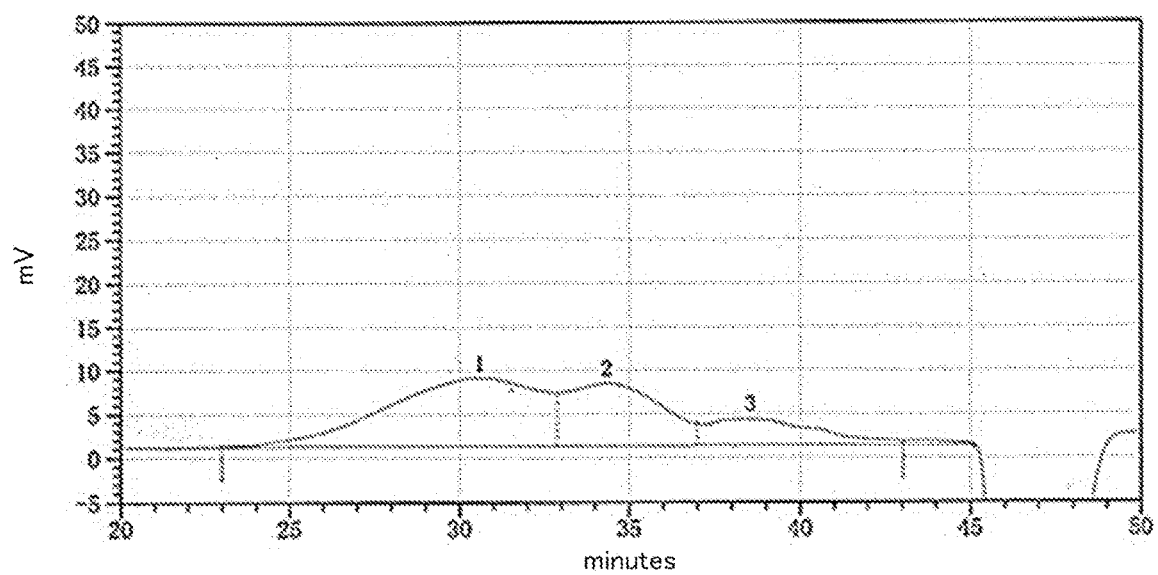
FIG. 8A plots a result of a gel permeation chromatograph (GPC) measurement of the component 1.
Figures 8B, 9, 10:
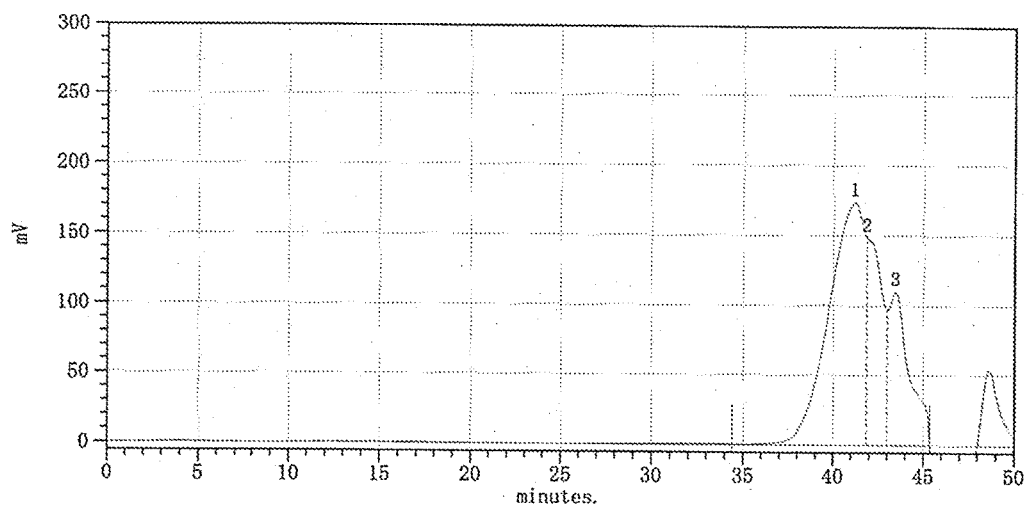
FIG. 8B plots a result of a gel permeation chromatograph (GPC) measurement of the component 2.
FIG. 9 is a diagram indicating an identification number of "intermediate jute No. 3" that may be used in the present invention.
FIG. 10 is a diagram indicating an identification number of "intermediate kenaf" that may be used in the present invention.

The identification number of the "intermediate jute No. 3" is indicated in FIG. 9. The identification number of the "intermediate kenaf" is indicated in FIG. 10.

The "intermediate jute No. 4" has the following properties.

Agricultural product type: Jute

<Extract Formed of Fractionated Component 1>

<<Method for Extracting Fractionated Component 1>>

Figure 2:
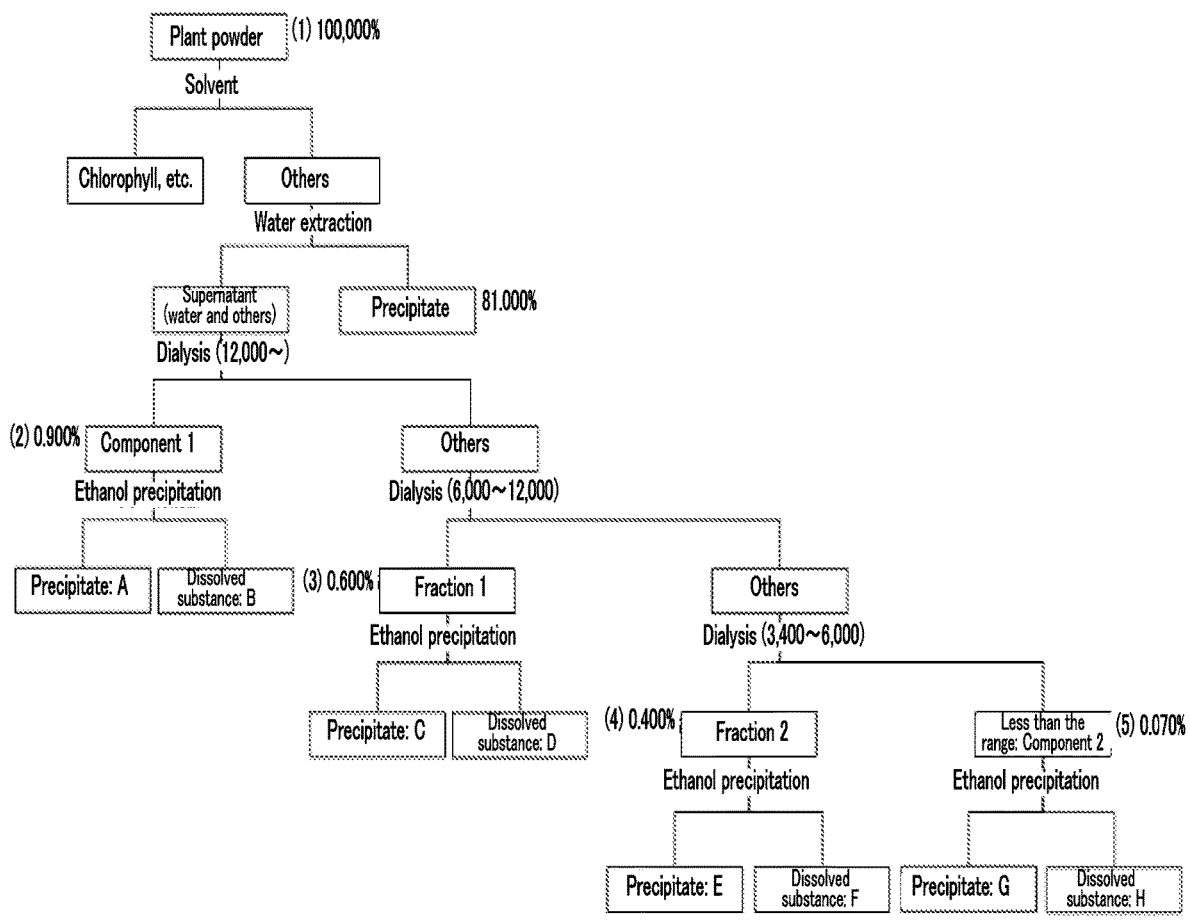
FIG. 2 is an image diagram illustrating a method for extracting the component 1 and the component 2.

The fractionated component 1 can be extracted according to a method illustrated in FIG. 2. Specifically, a dry plant is ground and subjected to extraction using ethyl acetate. Subsequently, the extraction residue is further subjected to extraction using distilled water, to obtain a supernatant. The supernatant is subjected to dialysis, to separate a component having a fractionation molecular weight of 12,000 or greater. In this way, the fractionated component 1 is obtained.

<<Result of Analysis of Fractionated Component 1>>

<<<Result of Analysis of Component A>>>

An ethanol-undissolved component (denoted by component A in FIG. 1) of the fractionated component 1 was measured by a Fourier transform infrared spectroscopy (FT-IR) method. The result of the measurement is plotted in FIG. 6A. This FT-IR measurement was performed with FTS-7000e/UMA600, VARIAN, and microscopic diamond cells. FT-IR measurements of a component B, a component G, and a component H described below were also performed under the same conditions.

Figure 6A:
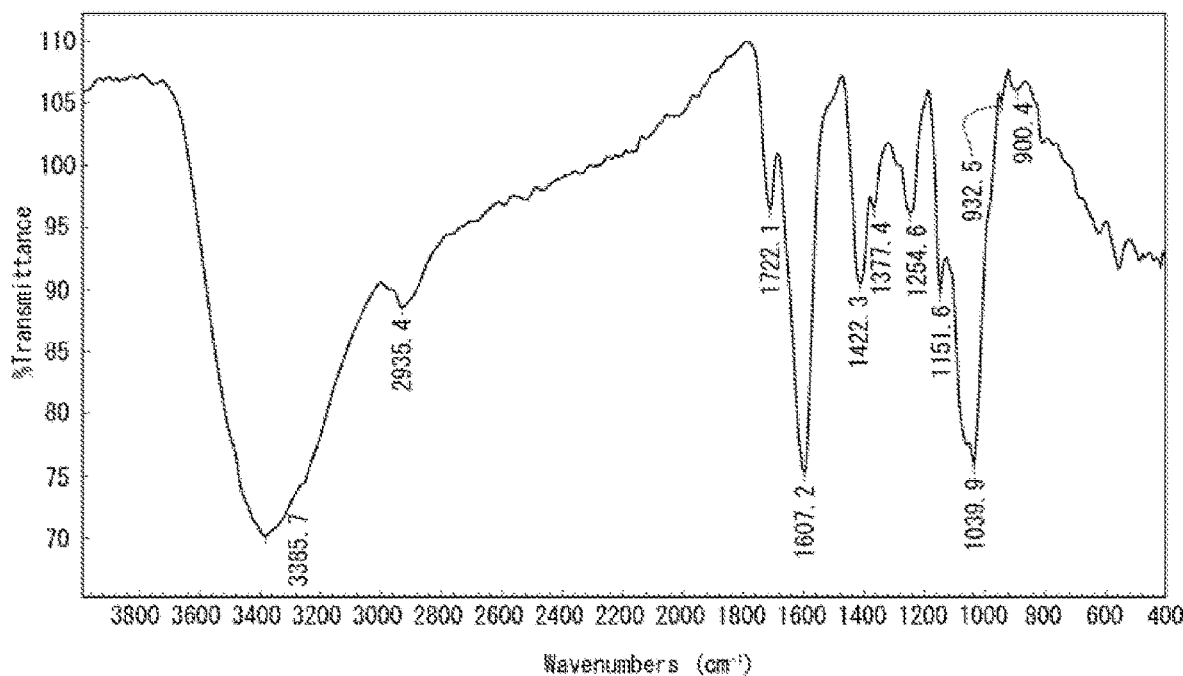
FIG. 6A plots a result of a Fourier transform infrared spectroscopy (FT-IR) measurement of an ethanol-undissolved component (component A) of the component 1.

As plotted in FIG. 6A, the component A exhibited peaks attributable to carboxylic acid in the FT-IR measurement. That is, the component A exhibited peaks near 1,700 $(cm^{-1})$ (ketone stretching) and near 1,600 $(cm^{-1})$ (amide stretching).

The component A was also measured by a gas chromatography mass spectrometry (GC-MS) method. The result of the measurement is plotted in FIG. 7A. This GC-MS measurement was performed with JMS-600H available from JEOL, using Ionization mode: EI+. GC-MS measurements of the component B, the component G, and the component H described below were also performed under the same conditions.

Figure 7A:
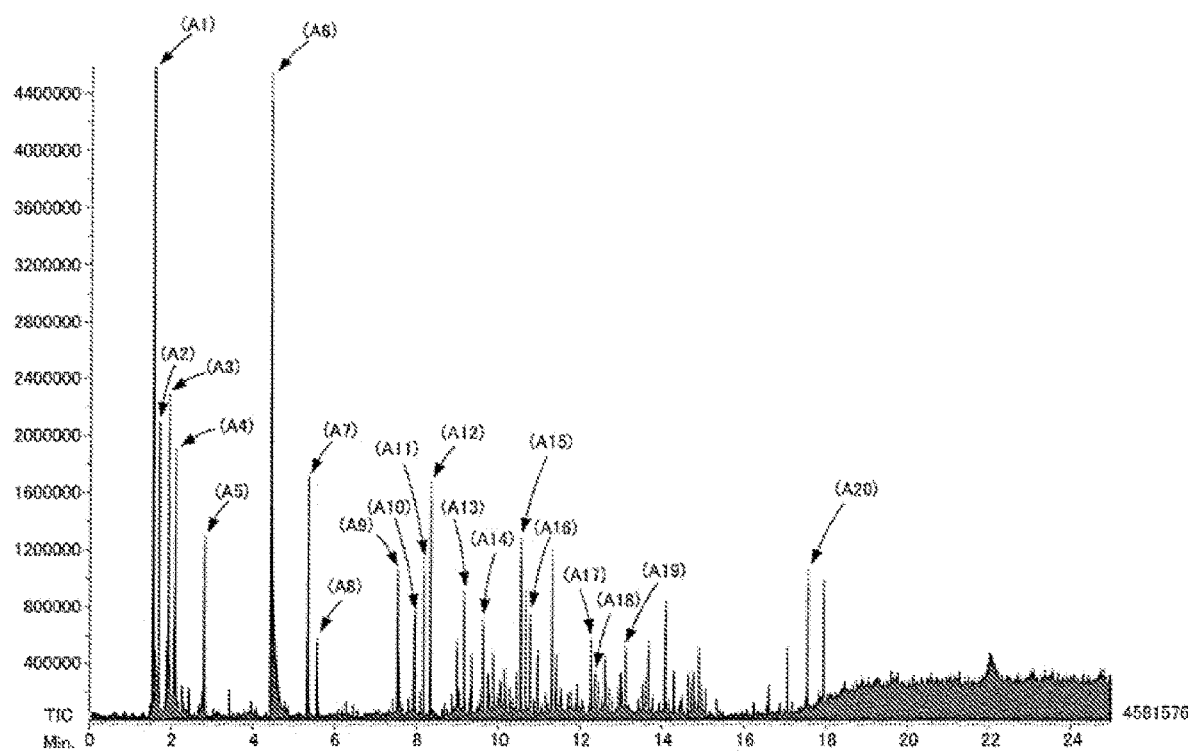
FIG. 7A plots a result of a gas chromatography mass spectrometry (GC-MS) measurement of the ethanol-undissolved component (component A) of the component 1.

As plotted in FIG. 7A, the component A exhibited peaks attributable to cellulose in the GC-MS measurement.

Attributions of the peaks (A1) to (A20) in FIG. 7A are estimated to be as follows.

(A1): $CO_2$
(A2): acetaldehyde
(A3) ○: ethanol
(A4) ○: acetylformaldehyde
(A5) ○: diacetyl
(A6) ○: acetic acid
(A7) ○: acetol
(A8) △: toluene
(A9) ○: acetoxyacetic acid
(A10) ○: 3-furaldehyde
(A11) ○: pyruvic acid methyl ester
(A12) ○: furfural (2-furaldehyde)

(A13) ○: the compound below

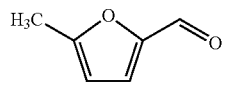

(A14) ○: the compound below

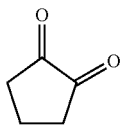

(A15) ○: the compound below

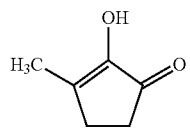

(A16) △: phenol
(A17) △: 4-pyridinol
(A18) △: cresol
(A19) △: indole
(A20): acetyl tributyl citrate The symbol "○" affixed to the above signs denotes a peak of a fragment attributable to cellulose.

The symbol "△" affixed to the above signs denotes a peak of a fragment attributable to gluten (plant protein).

<<<Result of Analysis of Component B>>

An ethanol-dissolved component (denoted by component B in FIG. 1) of the fractionated component 1 was measured by FT-IR. The result of the measurement is plotted in FIG. 6B.

Figure 6B:
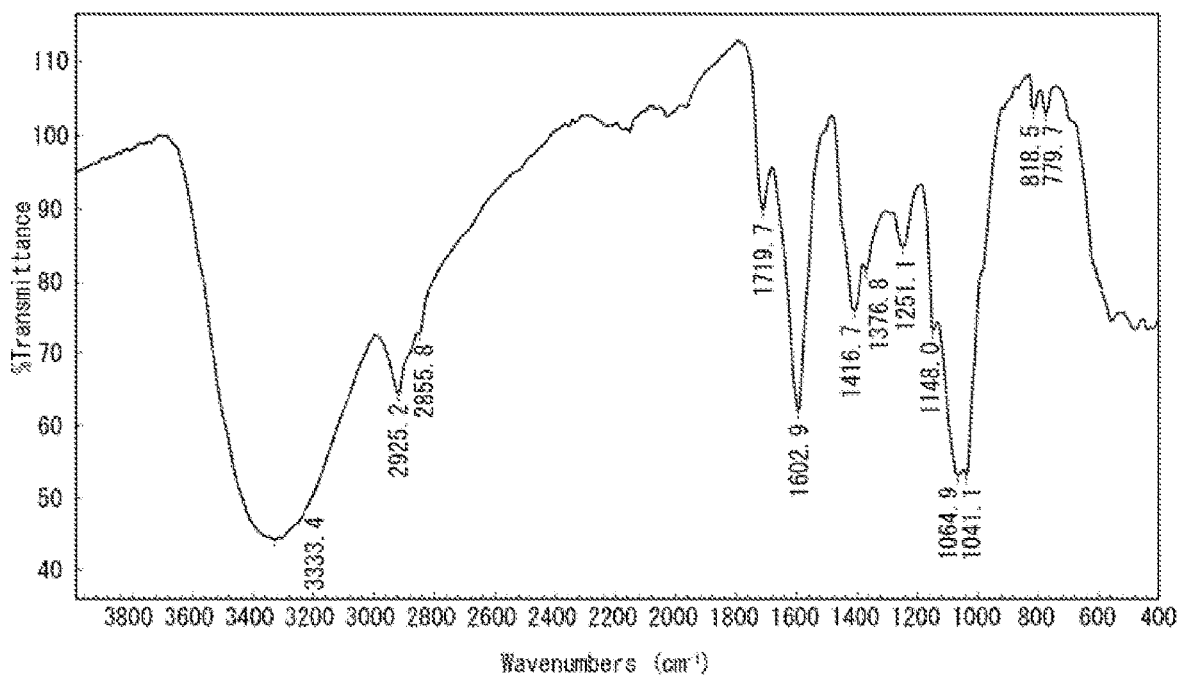
FIG. 6B plots a result of a Fourier transform infrared spectroscopy (FT-IR) measurement of an ethanol-dissolved component (component B) of the component 1.

As plotted in FIG. 6B, the component B exhibited peaks attributable to carboxylic acid in the FT-IR measurement. That is, the component B exhibited peaks near 1,700 ($cm^{-1}$) (ketone stretching) and near 1,600 ($cm^{-1}$) (amide stretching).

The component B was also measured by GC-MS. The result of the measurement is plotted in FIG. 7B.

Figure 7B:
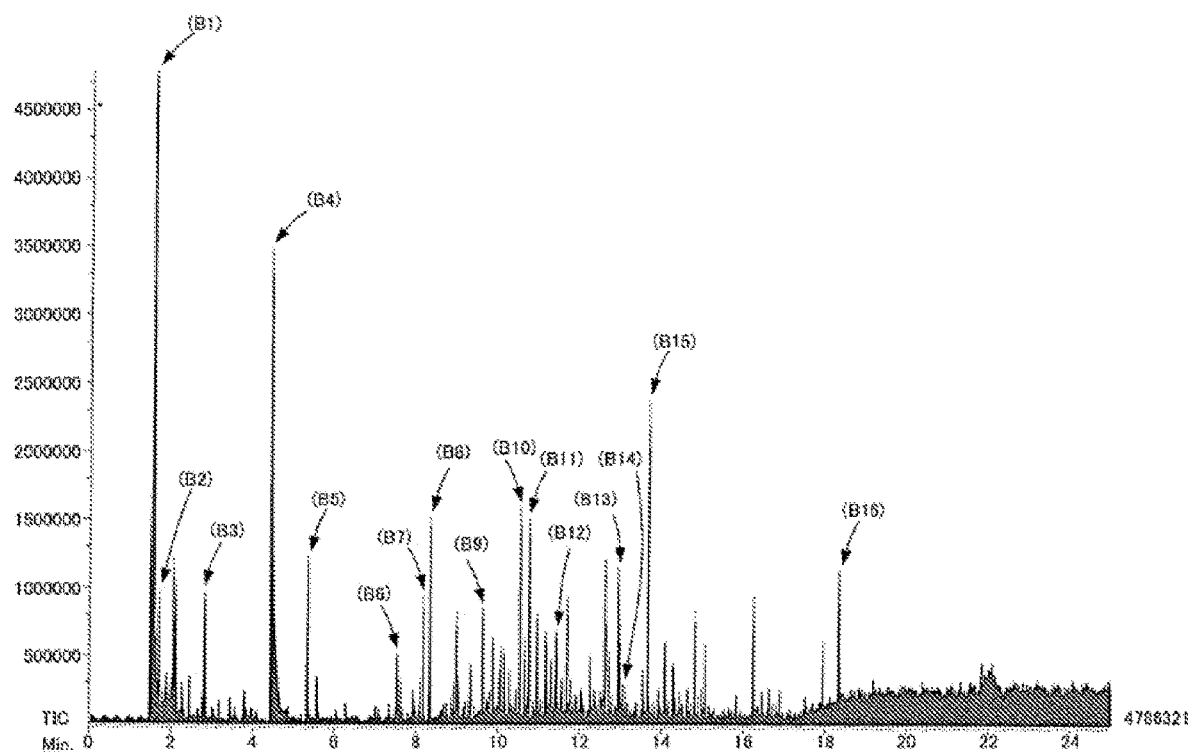
FIG. 7B plots a result of a gas chromatography mass spectrometry (GC-MS) measurement of the ethanol-dissolved component (component B) of the component 1.

As plotted in FIG. 7B, the component B exhibited peaks attributable to a plant protein in the GC-MS measurement.

Attributions of the peaks (B1) to (B16) in FIG. 7B are estimated to be as follows.

(B1): $CO_2$
(B2): acetaldehyde
(B3) ○: diacetyl
(B4) □: acetic acid
(B5) ○: the compound below

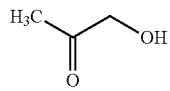

(B6) □: acetic anhydride
(B7) ○: pyruvic acid methyl ester
(B8) ○: furfural (2-furaldehyde)

(B9) ○: the compound below

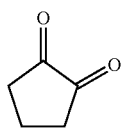

(B10) ○: the compound below

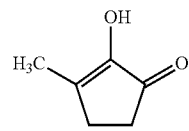

(B11) △: phenol
(B12) △: cresol
(B13) ○: the compound below

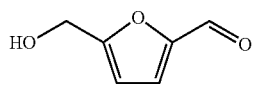

(B14) △: indole
(B15): hydroquinone
(B16): oleamide

The symbol "○" affixed to the above signs denotes a peak of a fragment attributable to cellulose.

The symbol "□" affixed to the above signs denotes a peak of a fragment attributable to cellulose acetate.

The symbol "△" affixed to the above signs denotes a peak of a fragment attributable to gluten (plant protein).

From the results of the FT-IR measurements and the GC-MS measurements of the component A and the component B, the component 1 is considered to be formed of uronic acid or carboxylic acid that has a structure similar to galacturonic acid. Hence, the component 1 is considered to have inorganic ions adsorb thereto and exhibit an excellent effect in water purification.

The component 1 was also measured by gel permeation chromatograph (GPC). The result of the measurement is plotted in FIG. 8A. This GPC measurement was performed with GPC SYSTEM 21, Shodex, and TSKgel GMPW. GPC measurement of the component 2 described below was also performed under the same conditions.

From the result of FIG. 8A, it can be seen that the component 1 contains a substance having a weight average molecular weight (Mw) of 300,000 or greater by 50% (area) or greater.

<<Water-Purifying Action of Fractionated Component 1>>

An experiment of a water-purifying action was performed using the extract formed of the component 1. The result is plotted in FIG. 3.

Figure 3:
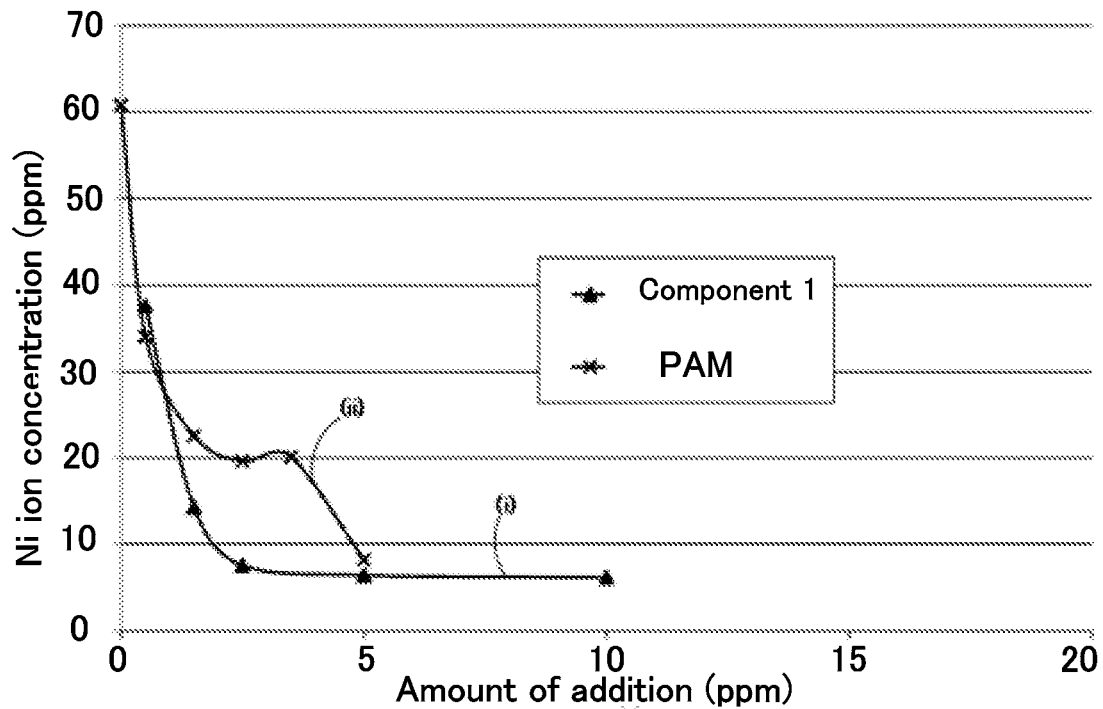
FIG. 3 is a graph plotting a result of an experiment of a water-purifying effect of the component 1.

In FIG. 3, (i) plots the change of the Ni ion concentration when the extract formed of the component 1 was directly added in water containing $N_i$. On the other hand, in FIG. 3, (ii) plots the change of the Ni ion concentration when a commercially available polymeric flocculant (polyacrylamide: PAM) was added as a water-purifying agent in water containing Ni.

From the result of FIG. 3, it was confirmed that the component 1 was able to improve the water quality (reduction in the Ni ion concentration) in a smaller amount than the PAM.

<Extract Formed of Fractionated Component 2>
<<Method for Extracting Fractionated Component 2>>

The fractionated component 2 can be extracted according to the method illustrated in FIG. 2. Specifically, a component having a fractionation molecular weight of less than 12,000, which was obtained by the dialysis described above, is further subjected to dialysis, to obtain a component having a fractionation molecular weight of less than 6,000, which is further subjected to dialysis, to obtain and separate a component having a fractionation molecular weight of less than 3,400. In this way, the fractionated component 2 is obtained.

<<Result of Analysis of Fractionated Component 2>>
<<<Result of Analysis of Component G>>

An ethanol-undissolved component (denoted by component G in FIG. 1) of the fractionated component 2 was measured by FT-IR. The result of the measurement is plotted in FIG. 6C.

Figure 6C:
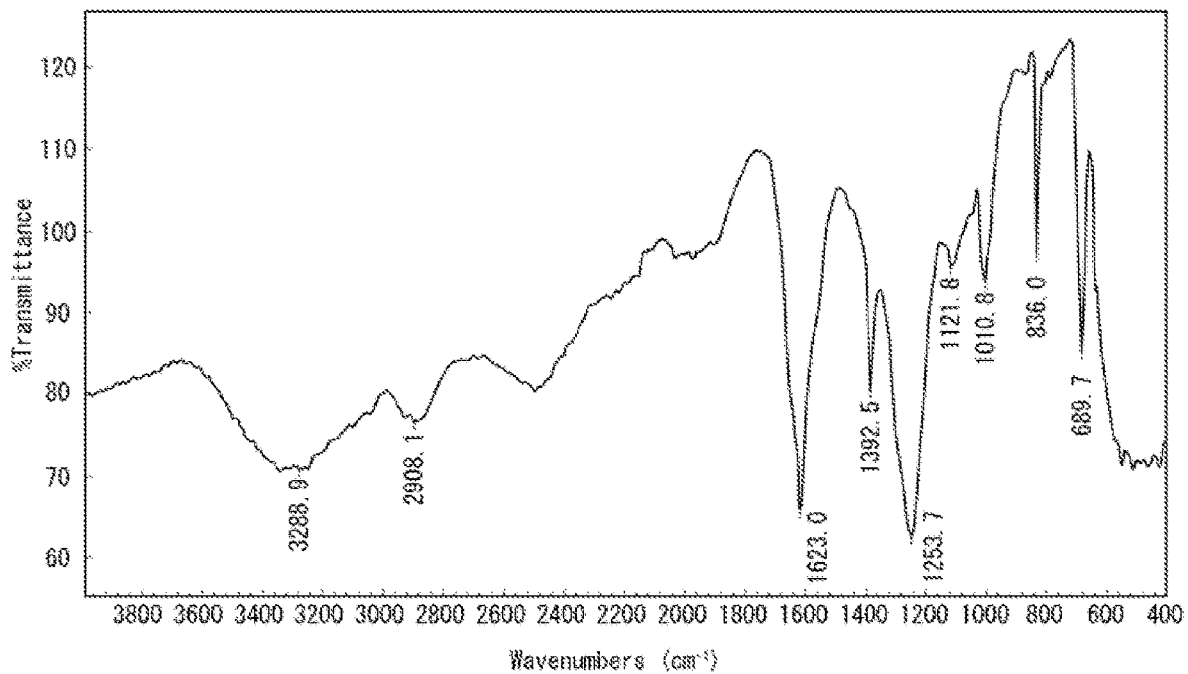
FIG. 6C plots a result of a Fourier transform infrared spectroscopy (FT-IR) measurement of an ethanol-undissolved component (component G) of the component 2.

As plotted in FIG. 6C, the component G exhibits peaks attributable to an amide group in the FT-IR measurement. That is, the component G exhibits main peaks in a range of from 1,590 (cm$^{-1}$) through 1,630 (cm$^{-1}$) (amide stretching).

The component G was also measured by GC-MS. The result of the measurement is plotted in FIG. 7C.

Figure 7C:
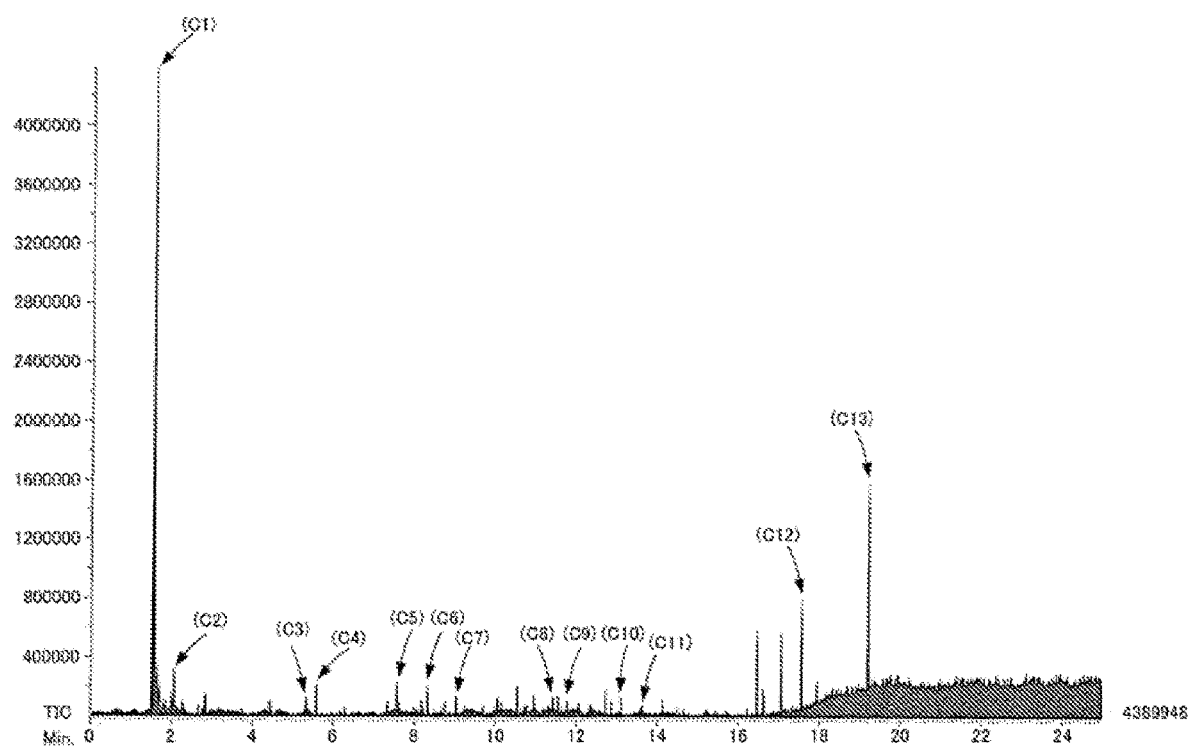
FIG. 7C plots a result of a gas chromatography mass spectrometry (GC-MS) measurement of the ethanol-undissolved component (component G) of the component 2.

As plotted in FIG. 7C, the component G exhibits peaks of 1,8-diazacyclotetradecane-2,7-dione in the GC-MS measurement.

Attributions of the peaks (C1) to (C13) in FIG. 7C are estimated to be as follows.

(C1): $CO_2$
(C2): acetone
(C3): acetol
(C4) Δ: toluene
(C5) ×: pyrrole
(C6): cyclopentanone
(C7): the compound below

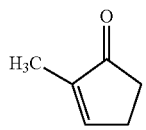

(C8) Δ: cresol
(C9) ×: 2-pyrrolidinone
(C10) ×: indole
(C11): hydroquinone
(C12): acetyltributyl citrate
(C13) ×: 1,8-diazacyclotetradecane-2,7-dione The symbol "×" affixed to the above signs denotes a peak of a fragment attributable to polysaccharide such as chitin and chitosan.

The symbol "Δ" affixed to the above signs denotes a peak of a fragment attributable to gluten (plant protein).

<<<Result of Analysis of Component H>>

An ethanol-dissolved component (denoted by component H in FIG. 1) of the fractionated component 2 was measured by FT-IR. The result of the measurement is plotted in FIG. 6D.

Figure 6D:
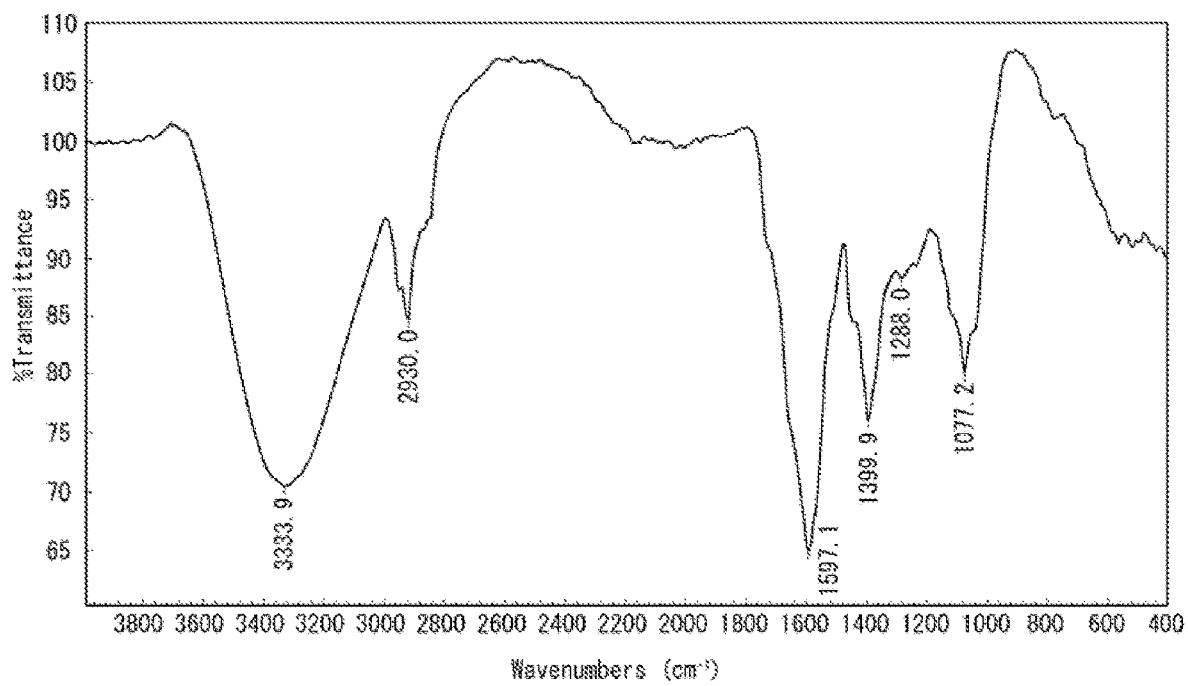
FIG. 6D plots a result of a Fourier transform infrared spectroscopy (FT-IR) measurement of an ethanol-dissolved component (component H) of the component 2.

As plotted in FIG. 6D, the component H exhibits peaks attributable to an amide group in the FT-IR measurement. That is, the component H exhibits main peaks in a range of from 1,590 (cm$^{-1}$) through 1,630 (cm$^{-1}$) (amide stretching).

The component H was also measured by GC-MS. The result of the measurement is plotted in FIG. 7D.

Figure 7D:
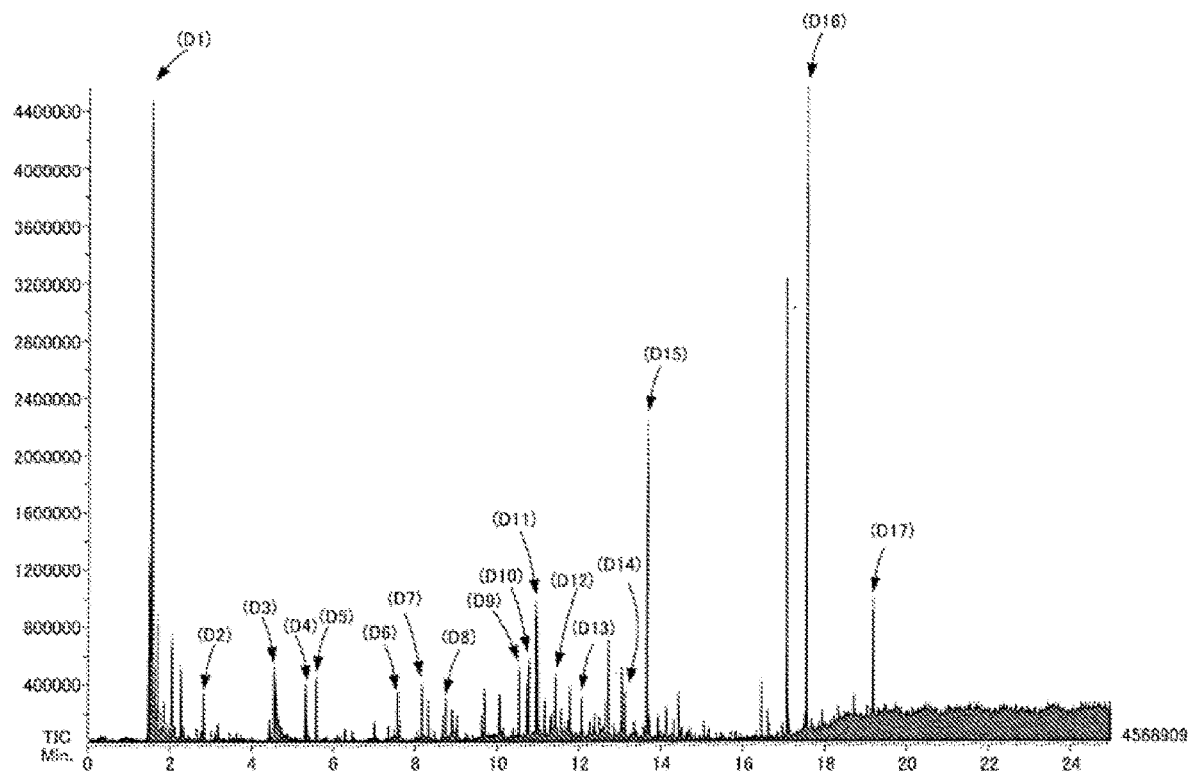
FIG. 7D plots a result of a gas chromatography mass spectrometry (GC-MS) measurement of the ethanol-dissolved component (component H) of the component 2.

As plotted in FIG. 7D, the component H exhibits peaks of 1,8-diazacyclotetradecane-2,7-dione in the GC-MS measurement.

Attributions of the peaks (DO to (D17) in FIG. 7C are estimated to be as follows.

(D1): $CO_2$
(D2): methyl ethyl ketone
(D3): acetic acid
(D4) ○: acetol
(D5) Δ: toluene
(D6) ×: pyrrole
(D7): styrene
(D8) ×: 2-methyl-1H-pyrrole
(D9) ×: the compound below

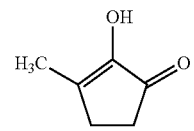

(D10) Δ: phenol
(D11): p-methoxytoluene
(D12) Δ: cresol
(D13): p-ethyl phenol
(D14)×: indole
(D15): hydroquinone
(D16): acetyl tributyl citrate
(D17) ×: 1,8-diazacyclotetradecane-2,7-dione The symbol "○" affixed to the above sign denotes a peak of a fragment attributable to cellulose.

The symbol "×" affixed to the above signs denotes a peak of a fragment attributable to polysaccharide such as chitin and chitosan.

The symbol "Δ" affixed to the above signs denotes a peak of a fragment attributable to gluten (plant protein).

Figure 4:
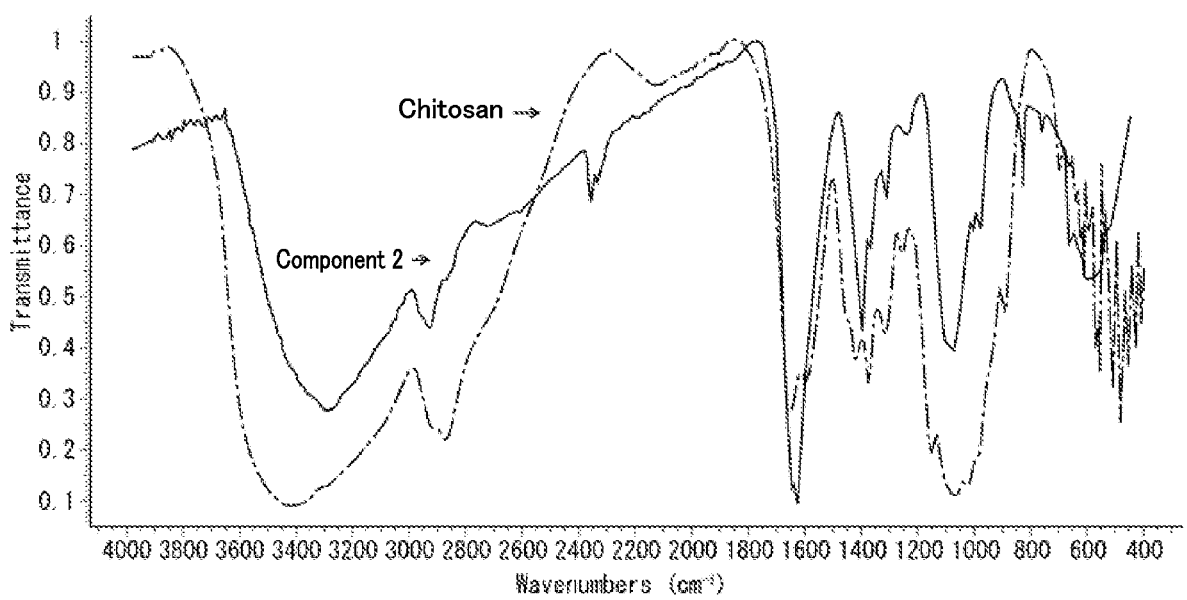
FIG. 4 plots a result of a microscopic IR measurement of the component 2.

The result of a microscopic infrared spectroscopy (microscopic IR) measurement in which the extract formed of the component 2 was compared with chitosan is plotted in FIG. 4.

From the results of the FT-IR measurements and the GC-MS measurements of the component G and the component H and the result of FIG. 4, the component 2 is considered to be a water-soluble chitosan. Chitosans (chitins) extracted from, for example, crustacean are typically water-insoluble, but water-soluble chitosan is considered to be effective in adsorption of inorganic ions.

In the present invention, water solubility means solubility of 50% by mass of greater in water.

The component 2 was also measured by GPC. The result of the measurement is plotted in FIG. 8B.

From the result of FIG. 8, it can be seen that the component 2 contains a substance having a weight average molecular weight (Mw) of from 200 through 2,500 by 90% (area) or greater.

<<Water-Purifying Action of Fractionated Component 2>>

An experiment of a water-purifying action was performed using the extract formed of the component 2. The result is plotted in FIG. 5.

Figure 5:
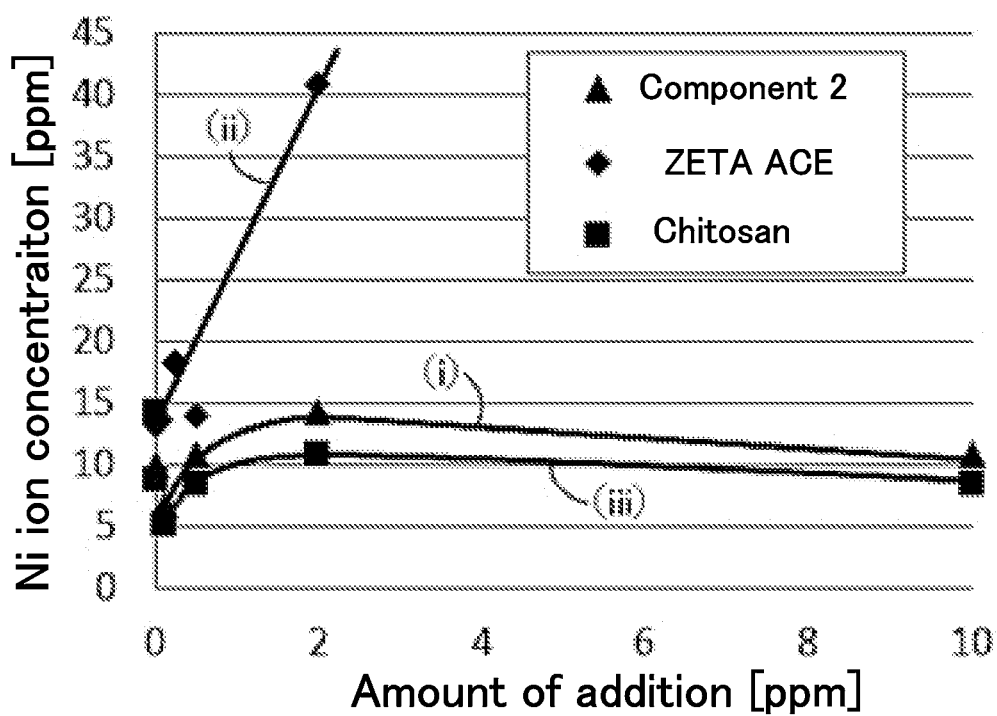
FIG. 5 is a graph plotting a result of an experiment of a water-purifying effect of the component 2.

In FIG. 5, (i) plots the change of the Ni ion concentration when the extract formed of the component 2 was directly added in water containing Ni. On the other hand, in FIG. 5, (ii) and (iii) plot the changes of the Ni ion concentration when a commercially available ZETA ACE as a flocculant and chitosan were added in water containing Ni.

From the results of FIG. 5, addition of ZETA ACE in a higher amount led to greater suppression of floc growth and a poorer water quality level, whereas the component 2 succeeded in improving the water quality (reducing the Ni ion concentration) regardless of the amount of addition. The component 2 is considered to exhibit a water-purifying effect based on a mechanism that cannot be explained only by the flocculating effect exhibited by ZETA ACE, i.e., a mechanism different from a zeta potential.

Moreover, as plotted in FIG. 5, the component 2 achieved a result similar to the case of adding chitosan in the wastewater. Also from this result, the component 2 is considered to be a chitosan.

(Water-Purifying Agent)

The water-purifying agent of the present invention contains a plant powder.

As the first mode of the water-purifying agent of the present invention, it is preferable that the plant powder contain the component 1 or the component 2, or both thereof, which is/are (Extract of plant powder) described above.

This is because an effective water-purifying action can be exhibited efficiently even if the amount of addition is small.

As the second mode of the water-purifying agent of the present invention, it is preferable that the water-purifying agent contain a plant powder that contains extracted component(s) formed of the component 1 or the component 2, or both thereof in predetermined effective amount(s).

<First Mode>

The water-purifying agent of the present invention contains the component 1 or the component 2, or both thereof extracted by the production method described above.

Particularly, it is preferable that the water-purifying agent of the present invention contain both of the component 1 and the component 2 extracted by the production method described above. As plotted in FIG. 3 and FIG. 5, it is inferred that the component 1 and the component 2 both have a water-purifying function but have different mechanisms of the water-purifying function. Hence, containing both of the components makes it possible to express the water-purifying function by a plurality of approaches. Therefore, a water-purifying agent containing both of the component 1 and the component 2 is more preferable.

<Second Mode>

The water-purifying agent of the present invention contains a plant powder containing extracted component(s) formed of the component 1 or the component 2, or both thereof.

Here, the component 1 is contained in the plant powder in an amount of 0.5% by mass or greater, more preferably in an amount of 0.7% by mass, and yet more preferably in an amount of 0.9% by mass as will be demonstrated by Examples.

The component 2 is contained in the plant powder in an amount of 0.05% by mass or greater, and more preferably in an amount of 0.07% by mass.

According to the flowchart illustrated in FIG. 2, the component 1 and the component 2 were extracted from a dried product of *Corchorus olitorius* including all leaves, stalks, and roots. As the yield of each extracted component, the result presented in Table 1 below was achieved as a result of one experiment example.

The numerals (1) to (5) in Table 1 correspond to the numerals (1) to (5) in FIG. 2. That is, when the raw material of the plant powder is regarded as 100 parts by mass, the component 1 was extracted in an amount of 0.9 parts by mass, and the component 2 was extracted in an amount of 0.07 parts by mass (see the results of (2) and (5) in Table 1).

Next, the component 1 and the component 2 were extracted from a dried product of *Corchorus olitorius* including only leaves. The results as the yields of the respective components are presented below (Table 2 below).

As can be seen from Table 1 below and Table 2 below, the yields of the component 1 and the component 2 vary depending on the plant powder, which is the raw material. Hence, it is preferable to appropriately adjust the contents of the component 1 and the component 2 to desired ranges respectively, by varying the ratio among leaves, stalks, and roots of the plant.

TABLE 1

| Fractionation of molecular weight | Yield of extracted component (relative to 100.00% of raw material (leaves, stalks, and roots) indicated by (1) in FIG. 2) |
| --- | --- |
| 12,000~ | 0.900% (indicated by (2) in FIG. 2) |
| 6,000~12,000 | 0.600% (indicated by (4) in FIG. 2) |
| 3,400~6,000 | 0.400% (indicated by (4) in FIG. 2) |
| ~3,400 | 0.070% (indicated by (5) in FIG. 2) |

TABLE 2

| Fractionation of molecular weight | Yield of extracted component (relative to 100.00% of raw material (only leaves) indicated by (1) in FIG. 2) |
| --- | --- |
| 12,000~ | 7.000% (indicated by (2) in FIG. 2) |
| 6,000~12,000 | 3.000% (indicated by (4) in FIG. 2) |
| 3,400~6,000 | 0.790% (indicated by (4) in FIG. 2) |
| ~3,400 | 5.666% (indicated by (5) in FIG. 2) |

<Other Additives>

In addition to the powder of the plant, the water-purifying agent may contain additives such as a polymeric flocculant, a filler, a thickener, a colorant, and a thixotropy imparting agent as other additives.

<<Polymeric Flocculant>>

The polymeric flocculant is not particularly limited so long as the polymeric flocculant exhibits an effect of removing the inorganic unnecessary substance in wastewater like the powder of the plant described above. Examples of the polymeric flocculant include polyacrylamide (PAM), a salt obtained by partially hydrolyzing polyacrylamide, sodium alginate, sodium polyacrylate, and CMC sodium salt. Among these polymeric flocculants, polyacrylamide is preferable for use. As the polyacrylamide, for example, commercially available products FLOPAN AN 956, FLOPAN AN 995SI-1, FA 920SH, FO 4490, and AN 923 (available from SNF Japan Co., Ltd.) can be used.

It is preferable that the ratio of the component 1 in the water-purifying agent that also contains the other additives such as the polymeric flocculant be 0.5% by mass or greater relative to the total amount of the water-purifying agent.

It is preferable that the ratio of the component 2 be 0.05% by mass or greater relative to the total amount of the water-purifying agent.

(Wastewater Treatment Method)

A wastewater treatment method of the present invention is for removing the inorganic unnecessary substance in wastewater by feeding the water-purifying agent of the present invention described above to the wastewater.

Examples of the inorganic unnecessary substance include an inorganic unnecessary substance that contains at least any one selected from the group consisting of nickel, fluorine, iron, copper, zinc, chromium, arsenic, cadmium, and lead.

The wastewater treatment method of the present invention will be specifically described.

For example, it is possible to add the water-purifying agent of the present invention after an insolubilizing step of adding a base to wastewater to make the wastewater basic, insolubilize at least part of the heavy metal ions, and form a suspended solid matter.

The water-purifying agent is fed to the wastewater to make the inorganic unnecessary substance flocculate and settle, and the settled, separated precipitate is removed. In this way, the wastewater is purified.

EXAMPLES

The present invention will be described below by way of Examples. The present invention should not be construed as being limited to these Examples.

Example 1

As the plant, "intermediate jute No. 4", which was *Corchorus olitorius* having an identification number 2013 in Institute of Bast Fiber Crops, Chinese Academy of Agricultural Sciences, was used.

A dried product (containing the component 1 in an amount of 0.56% by mass) of a plant including all leaves, stalks, and roots of the intermediate jute No. 4 (with a ratio of the leaves in the plant of 8% by mass) was used.

The intermediate jute No. 4 was dried and ground, and then separated through a sieve, in order to use a product with a size of 250 micrometers or less.

The component 1 being contained in an amount of 0.56% by mass in the dried product of the intermediate jute No. 4 used in the present Example was confirmed by performing the extracting operation described below.

That is, ethyl acetate was added to the dried product of the intermediate jute No. 4, to obtain a 10% by mass solution, which was left to stand still at room temperature (23 degrees C.) for 8 hours, followed by filtration through a filter paper. The residue was washed with ethyl acetate, and then further subjected to extraction using distilled water, to obtain a supernatant, which was subjected to dialysis to separate a component having a fractionation molecular weight of 12,000 or greater, to obtain the component 1. Then, the ratio of the component 1 relative to the dried product of the intermediate jute No. 4, which was the raw material, was calculated.

To wastewater containing nickel, $FeCl_3$ was added by 250 ppm as a primary flocculant, and then the water-purifying agent containing the dried product of *Corchorus olitorius* containing the component 1 in an amount of 0.56% by mass was added.

The initial Ni ion concentration was 60 ppm.

The result of the nickel ion concentration when the water-purifying agent of the present invention was added is presented in Table 3 below. As presented in Table 3, reduction in the nickel ion concentration was confirmed. With a nickel ion concentration of 8 ppm or lower, it can be judged that the water-purifying agent is non-problematic in practical use.

Example 2

An experiment was performed in the same manner as in Example 1, except that unlike in Example 1, the dried product of the intermediate jute No. 4 was changed to a dried product with a ratio of leaves of 10% by mass (containing the component 1 in an amount of 0.7% by mass). As presented in Table 3 below, reduction in the nickel ion concentration was confirmed in Example 2.

Example 3

An experiment was performed in the same manner as in Example 1, except that unlike in Example 1, the dried product of the intermediate jute No. 4 was changed to a dried product with a ratio of leaves of 100% by mass (containing the component 1 in an amount of 7.0% by mass). As presented in Table 3 below, reduction in the nickel ion concentration was confirmed in Example 3.

Comparative Example 1

An experiment was performed in the same manner as in Example 1, except that unlike in Example 1, the dried product of the intermediate jute No. 4 was changed to a dried product mainly containing stalks and roots but free of leaves (containing the component 1 in an amount of 0.1% by mass). As presented in Table 3 below, reduction in the nickel ion concentration was poor in Comparative Example 1.

Comparative Example 2

An experiment was performed in the same manner as in Example 1, except that unlike in Example 1, the dried product of the intermediate jute No. 4 was changed to a dried product with a ratio of leaves of 3% by mass (containing the component 1 in an amount of 0.21% by mass). As presented in Table 3 below, a sufficient reduction in the nickel ion concentration was not achieved in Comparative Example 2.

Comparative Example 3

An experiment was performed in the same manner as in Example 1, except that unlike in Example 1, the dried product of the intermediate jute No. 4 was changed to a dried product with a ratio of leaves of 5% by mass (containing the component 1 in an amount of 0.35% by mass). As presented in Table 3 below, a sufficient reduction in the nickel ion concentration was not achieved in Comparative Example 3.

Example 4

An experiment was performed in the same manner as in Example 1, except that unlike in Example 1, an extract formed of the component 1, extracted from the dried product of the intermediate jute No. 4, was used instead of the dried product of the intermediate jute No. 4, and this extract was directly added in an amount of 50 ppm. As presented in Table 3 below, reduction in the nickel ion concentration was confirmed in Example 4.

Example 5

An experiment was performed in the same manner as in Example 4, except that unlike in Example 4, the extract formed of the component 1, extracted from the dried product of the intermediate jute No. 4, was added with the amount of addition changed to 5 ppm. As presented in Table 3 below, an excellent reduction in the nickel ion concentration that is the same as in Example 4 was confirmed with even such a small amount of addition.

Example 6

An experiment was performed in the same manner as in Example 1, except that unlike in Example 1, as the kind of the plant, "intermediate jute No. 3", which was *Corchorus olitorius* having an identification number in Institute of Bast Fiber Crops, Chinese Academy of Agricultural Sciences, i.e., varieties identification of registration No. 1209006 in Anhui province, was used instead of the intermediate jute No. 4.

Although the nickel ion concentration reducing effect was better in Example 1, a good nickel ion concentration reducing effect, which was almost the same as in Example 1, was exhibited in Example 6.

TABLE 3

| | Part of plant | Amount of water-purifying agent added (ppm) | Content of component 1 in plant (% by mass) | Ni ion concentration after treatment (ppm) |
| --- | --- | --- | --- | --- |
| Comp. Ex. 1 | Other than leaves | 50 | 0.1 | 35 |
| Comp. Ex. 2 | 3% by mass of leaves | 50 | 0.21 | 15 |
| Comp. Ex. 3 | 5% by mass of leaves | 50 | 0.35 | 10 |
| Ex. 1 | 8% by mass of leaves | 50 | 0.56 | 6 |
| Ex. 2 | 10% by mass of leaves | 50 | 0.7 | 5.6 |
| Ex. 3 | 100% by mass of leaves | 50 | 7.0 | 5 |
| Ex. 4 | Component 1 | 50 | 100 | Lower than 5 |
| Ex. 5 | Component 1 | 5 | 100 | Lower than 5 |

The invention claimed is:

1. A water-purifying agent, comprising:
an extract, being formed of:
a fractionated component 1 of a water extract of a plant powder and a polymeric flocculant,
wherein the fractionated component 1 is a fractionated component having a fractionation molecular weight of 12,000 or greater,
wherein an ethanol-undissolved component of the fractionated component 1 exhibits a peak attributable to carboxylic acid in a Fourier transform infrared spectroscopy (FT-IR) measurement and exhibits a peak attributable to cellulose in a gas chromatography mass spectrometry (GC-MS) measurement,
wherein an ethanol-dissolved component of the fractionated component 1 exhibits a peak attributable to carboxylic acid in the FT-IR measurement and exhibits a peak attributable to a plant protein in the GC-MS measurement, and
wherein the water extract of a plant powder is a water extract of ethyl acetate extraction residue of a plant powder.

2. The water-purifying agent according to claim 1, wherein the polymeric flocculant is polyacrylamide.

3. A wastewater treatment method, comprising:
feeding the water-purifying agent according to claim 1 to wastewater, to remove an inorganic unnecessary substance in the wastewater.

4. The wastewater treatment method according to claim 3, wherein the wastewater is wastewater that comprises the inorganic unnecessary substance that comprises at least any one selected from the group consisting of nickel, fluorine, iron, copper, zinc, chromium, arsenic, cadmium, tin, and lead.

5. The water-purifying agent according to claim 1, wherein the plant powder is derived from Corchorus olitorius, and wherein the plant powder comprises 8% by mass or more of leaves.

6. A wastewater treatment method, comprising:
feeding the water-purifying agent according to claim 5 to wastewater, to remove an inorganic unnecessary substance in the wastewater.

* * * * *